United States Patent
Schlottig et al.

(10) Patent No.: US 9,050,391 B2
(45) Date of Patent: *Jun. 9, 2015

(54) IMPLANT AND PRODUCTION METHOD FOR SAID IMPLANT

(75) Inventors: Falko Schlottig, Füllinsdorf (CH); Matthias Schnabelrauch, Jena (DE); Armin Rex Kautz, Jena (DE)

(73) Assignee: NEXILIS AG, Grenchen (CH)

( * ) Notice: Subject to any disclaimer, the term of this patent is extended or adjusted under 35 U.S.C. 154(b) by 1130 days.

This patent is subject to a terminal disclaimer.

(21) Appl. No.: 12/091,902

(22) PCT Filed: Oct. 17, 2006

(86) PCT No.: PCT/CH2006/000576
§ 371 (c)(1),
(2), (4) Date: Apr. 28, 2008

(87) PCT Pub. No.: WO2007/048263
PCT Pub. Date: May 3, 2007

(65) Prior Publication Data
US 2008/0286328 A1 Nov. 20, 2008

(30) Foreign Application Priority Data
Oct. 27, 2005 (CH) ........................ 1724/05

(51) Int. Cl.
*A61L 27/54* (2006.01)
*A61F 2/00* (2006.01)
*A61L 27/32* (2006.01)

(52) U.S. Cl.
CPC ............ *A61L 27/32* (2013.01); *A61L 27/54* (2013.01); *A61L 2300/112* (2013.01); *A61L 2300/606* (2013.01)

(58) Field of Classification Search
None
See application file for complete search history.

(56) References Cited

U.S. PATENT DOCUMENTS

| 4,980,171 | A | * | 12/1990 | Fels et al. | 424/473 |
| 5,733,564 | A | * | 3/1998 | Lehtinen | 424/423 |
| 6,214,049 | B1 | * | 4/2001 | Gayer et al. | 623/16.11 |
| 6,905,723 | B2 | * | 6/2005 | Li | 427/2.27 |
| 6,913,764 | B2 | * | 7/2005 | Vogt et al. | 424/423 |

FOREIGN PATENT DOCUMENTS

| JP | 2000070288 A | 3/2000 |
| WO | 02/03963 A1 | 1/2002 |
| WO | 02/098307 A1 | 12/2002 |
| WO | WO 02098307 A1 * | 12/2002 |
| WO | 2005/018699 A1 | 3/2005 |
| WO | WO 2005018699 A1 * | 3/2005 |
| WO | WO 2005094784 A2 * | 10/2005 |

OTHER PUBLICATIONS

Daniel Buser, Titanium for Dental Applications (II): Implants with Roughened Surfaces, University of Berne, School of Dental Medicine, pp. 876-888, 2001.
M. Yoshinari, et al., Bone Response to Calcium Phophate-Coated and Bisphosphonate-Immobilized Titanium Implants, Dec. 5, 2001, pp. 2879-2885.
Hiroshi Kajiwara, et al., The Bisphosphonate Pamidronate on the Surface of Titanium Stimulates Bone Formation Around Tibial Implants in Rats, Biomaterials, Feb. 19, 2004, pp. 581-587.
Implant, Roche Lexikon & Fischer, Munchen-Jena 2003 (1984, 1987, 1993, 1999, 2003), Urban & Fischer, Munchen.
Weocjamg Xie, et al., In Vivo Evaluatin of Plasma-Sprayed Titanium Coating After Alkali Modification, Biomaterials, Sep. 2, 2004, pp. 3029-3037.
Jorg Hausleiter, et al., Prevention of Restenosis by a Novel Drug-Eluting Stent System With a Dose-Adjustable, Polymer-Free, On-Site Stent Coating, European Heart Journal (2005) pp. 26,1475-1481.
M.J. Raschke, et al., Biologisierung Von Implantaten in Der Chirurgie Des Stutz-Und Bewegungsapparates, (2004), pp. 653-663.
Ke Duan, et al., Electrolytic Deposition of Calcium Etidronate Drug Coating on Titanium Substrate, Department of Materials Engineering University of British Columbia, 2004.

* cited by examiner

*Primary Examiner* — Susan Tran
*Assistant Examiner* — William Craigo
(74) *Attorney, Agent, or Firm* — Sughrue Mion, PLLC

(57) ABSTRACT

The invention relates to an implant, e.g. a stent, bone replacement material, a prosthesis, a scaffold or similar, which comprises a coating at least in those surface areas that come into contact with hard and/or soft tissue when implanted. To ensure that the active ingredient contained in the coating (bisphosphonate) is released into the surrounding tissue or can act in the latter in a controlled manner at the correct speed, the coating is characterized in that it contains bisphosphonate, the respective pharmaceutically compatible salts or esters of the latter, in addition to at least one amphiphilic component, selected from the group containing branched or linear, substituted or unsubstituted, saturated or partially unsaturated C10-C30 alkyl-, alkenyl, alkylaryl-, aryl-, cycloalkyl-, alkylcycloalkyl-, alkylcycloaryl-carboxylates, -phosphates or -sulfates or mixtures thereof and/or a water-soluble ionic polymer component. The invention also relates to a method for producing an implant of this type and to a specific composition, which can be used to produce a coating of this type.

19 Claims, 1 Drawing Sheet

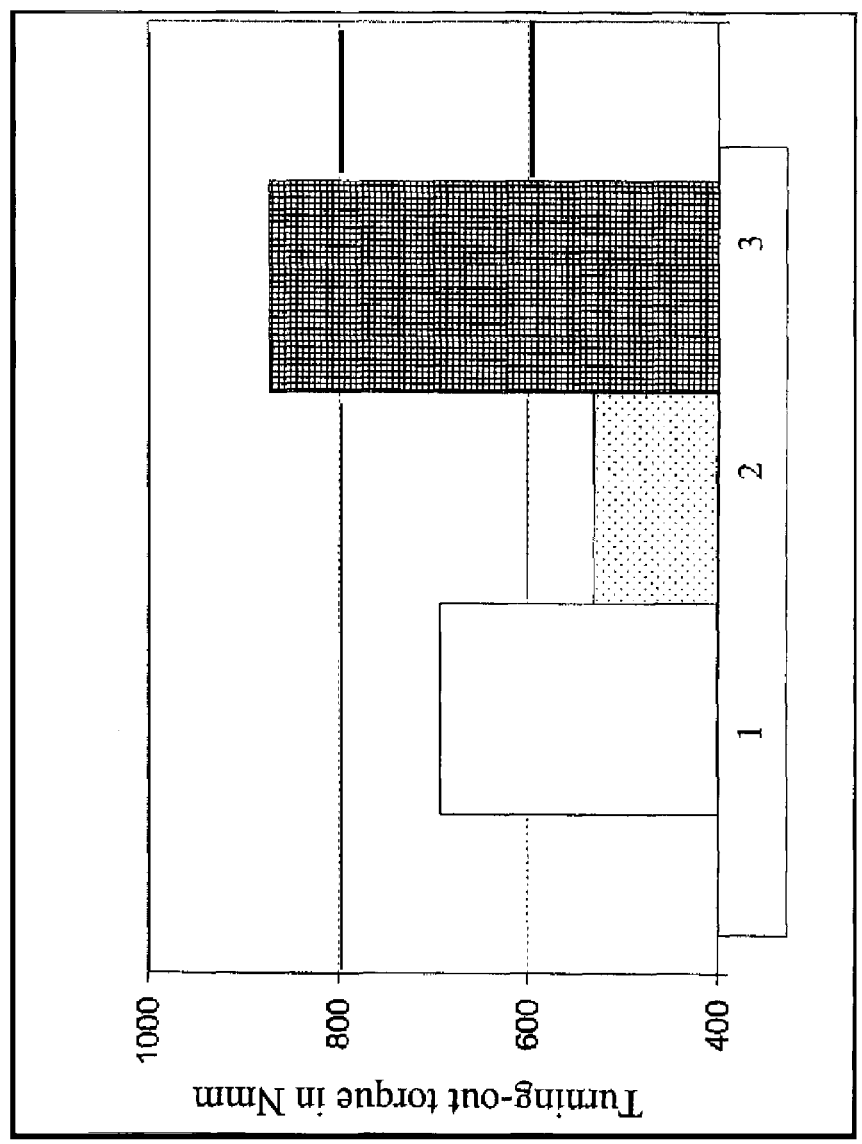

IMPLANT AND PRODUCTION METHOD FOR SAID IMPLANT

TECHNICAL FIELD

The present invention concerns an implant, which in at least some areas is provided with a coating in surface areas which in an implanted state are in contact with hard and/or soft tissue.

BACKGROUND OF THE INVENTION

Injured or damaged parts of the hard and/or soft tissue of the human body are restored or mechanically reinforced the best by using autologous hard and/or soft tissue. This is not always possible for various reasons, which is why in many cases synthetic material is used as a temporary (biodegradable or post-operatively removable) or permanent replacement material.

Implants which are anchored in the hard and/or soft tissue serve the temporary or permanent replacement or the support of parts of the human body which have been impaired by accident, abrasion, deficiency or sickness or otherwise degenerated. Normally, an implant is referred to as an artificial, chemically stable material which is introduced into the body as a plastic replacement or for mechanical reinforcement (see e.g. Roche Lexikon Medizin, Urban & Fischer (Eds.); $5^{th}$ edn. 2003). The support- and replacement function in the body is taken over on the basis of the mechanical characteristics and the implant design. Therefore, for instance the hip- and knee joint prostheses, spinal implants and vessel prostheses have been successfully used clinically for many years. For the anchoring of the implant and the implant tolerance at the interface implant surface/neighboring tissue, the implant surface has a great significance. By a change of the implant surface, the recovery process can be accelerated.

Various methods are used for surface treatment and surface structuring, as e.g. Titanium in Medicine, Material Science, Surface Science, Engineering, Biological Responses and Medical Applications Series: Engineering Materials, (Brunette, D. M.; Tengvall, P.; Textor, M.; Thomsen, P. (Eds.)); and the references cited therein.

The increase of roughness is for example well established (for many, see Titanium in Medicine, Material Science, Surface Science, Engineering, Biological Responses and Medical Applications Series: Engineering Materials, (Brunette, D. M.; Tenvall, P.; Textor, M.; Thomsen, P. (Eds.)).

Furthermore, papers exist which describe the chemical modification of implant surfaces in order to achieve a better connection of the bone to the implant surface (Xue W., Liu X, Zheng X, Ding C, Biomaterials. 2005 June; 26 (16): 3029-37).

More recent approaches are pharmaceutical modifications of the surface in order to accelerate the osseointegration of the implants and/or to promote or to stimulate the regeneration of the surrounding hard and/or soft tissue, e.g. with growth factors (Raschke M J, Schmidmaier G. Unfallchirurg. 2004 August; 107(8): 653-63).

By contrast, layers loaded with active substances can serve to prevent unwished reactions to implants, for example vessel prostheses (Hausleiter J, et al., Eur. Heart J. 2005 August; 26(15): 1475-81. Epub 2005 Jun. 23).

Other medication groups interesting for pharmaceutical surface modification are pharmaceuticals which were developed for the systemic treatment of osteoporosis, as for example calcitonin, strontiumranelate and various bisphosphonates.

Bisphosphonates can be interpreted as structural analogs of pyrophosphate, in which the P-O-P-group is replaced by an enzymatically stable P-C-P-group. By substitution of the hydrogen atoms at the C-atom of the P-C-P-group, bisphosphonates with various structural elements and characteristics are available. Known bisphosphonates which have been approved for clinical use are e.g. pamidronic acid, alendronic acid, ibandronic acid, clodronic acid or etidronic acid. In medicine, bisphosphonates have been established in the treatment of metabolic bone diseases, especially tumor-associated hypercalcemias, osteolytic bone metastases and postmenopausal and glucocortico-induced osteoporoses. Furthermore, tests show that bisphosphonates can be used for the prevention or for the treatment of vascular restenosis (WO 02/003677).

Depending on their structure, some of the known bisphosphonates clearly differ among each other with respect to their therapeutic efficacy. Especially those bisphosphonates which have an amino-function between the two phosphorus-atoms in the structural unit have a high therapeutic efficacy. Below, these compounds are referred to as amino-bisphosphonates.

The pharmacological action of the bisphosphonates is based on a high affinity to calcium phosphate structures of the bone surface, wherein subsequently bone-degrading cells (osteoclasts) are inhibited, which leads to a decrease of the bone resorption and simultaneously to a reactivation of bone-developing cells (osteoblasts). Due to the special pharmacokinetics of the bisphosphonates, a local therapy is preferred compared to the systemic administration.

Based on this knowledge, in the past years, numerous tests were conducted in which the immobilisation of selected bisphosphonates on hard tissue implants and their impact on the ingrowth-behavior of the corresponding implant were tested.

Thus, e.g. in U.S. Pat. No. 5,733,564 the coating of materials (endoprostheses, screws, pins, etc.) with aqueous bisphosphonate-solutions were described with the aim to accelerate the bone-regeneration around the implant. However, the poor adhesion of the bisphosphonates on metallic surfaces and their solubility in water constitute a disadvantage of this approach.

Yoshinari et al. (Biomaterials 23 (2002), 2879-2885) showed by means of in vivo studies that calciumphosphate-coated implants of pure titanium, which had been impregnated with an aqueous pamidronate-solution, showed an improved osteogenesis at the implant surface compared to implants which had not been impregnated with pamidronate. Due to the high affinity of the bisphosphonates to calcium ion-containing substrates, calciumphosphate surfaces constitute a possible substrate for the immobilisation of bisphosphonates, as on these surfaces the bioavailability of the bisphosphonates and thus their therapeutical efficacy by their interaction with calcium ions is present at a higher rate than on surfaces essentially free of calcium ions.

WO-A-02/04038 describes a further variant of the immobilisation of bisphosphonates in hydroxyapatite-containing coatings of bone implants. Because metallic implants play a dominating role in the hard tissue area and on the other hand a calcium phosphate coating of metallic surfaces entails increased production expenses, in the past, numerous attempts were made to modify metallic implant materials such that an effective bisphosphonate-immobilisation is enabled thereon.

Therefore, studies became known in which calcium ions are brought into the surface of titanium implants by electron beam-implantation (JP 2000070288, H. Kajiwara et al. Biomaterials 26 (2005), 581-587), in order to achieve an improved adhesion of bisphosphonates. However, this method has the disadvantage of high apparatus-related expenses.

Further studies concern the electrolytic separation of calcium-etidronate on pure titanium (K. Duan et al., J. Biomed. Mater. Res.: Appl. Biomater. 72B (2005), 43-51), wherein on the one hand thin films of bisphosphonate were able to be separated, however, they showed inhomogeneities and signs of shrinking during the drying process.

In WO-A-2005/018699, bisphosphonate-coated metallic implants are described, which were produced in a way that first, a protein layer, for example of fibrinogen is immobilized on the metallic surface. Subsequently, one or more bisphosphonates are covalently bound to this protein layer via reactive functional groups. A significant disadvantage of this method lies in the use of toxic reagents during the immobilisation or cross-linking, respectively, of the protein layer and the covalent coupling of the bisphosphonate.

SUMMARY OF THE INVENTION

One object of the invention is therefore, among others, to provide an improved implant, which e.g. shows a good and complication-free osteointegration, and which still can be produced in a simple and cost-efficient process.

One solution to this is for instance achieved in that at least in some areas the implant is provided with a coating in surface areas which in an implanted state are at least indirectly in contact with hard and/or soft tissue. At least indirectly in contact herein means that the coating can be in direct contact with the hard and/or the soft tissue, or over channels, openings, and/or a further layer or layers, which however do not or only marginally influence or change, respectively, the release characteristics of the bisphosphonate described below. This coating contains at least a bisphosphonate of the general formula $(H_2O_3P)$—$CXY$—$(PO_3H_2)$, wherein X is selected from H, OH, Cl, F, or a methyl group, Y is selected from H, Cl, F, $NH_2$, or a linear or a branched C1-C20 alkyl group (preferably C1-C10, more preferably C1-C7), which is unsubstituted or preferably substituted by $NH_2$, $N(CH_3)_2$, $NH(CH_3)$, $N(CH_3)_3$, pyridinyl or imidazolyl, wherein one or more carbon atoms can be replaced by hetero atoms selected from the group —$NR^1$—, —S— or —O—, wherein $R^1$ is selected from —H or —$CH_3$, with the proviso that no two hetero atoms are interconnected, or pharmaceutically compatible salts or esters of the latter, in addition to at least one amphiphilic component selected from the group of branched or linear, substituted or unsubstituted, saturated or partially unsaturated C10-C30 alkyl-, alkenyl-, alkylaryl-, aryl-, cycloalkyl-, alkylcycloalkyl-, alkylcykloaryl-carboxylates, -phosphates, or -sulfates or mixtures thereof, and/or a water-soluble ionic polymeric component.

Also mixtures of various such bisphosphonates are possible, as well as mixtures of various amphiphilic components, or water-soluble ionic polymeric components, respectively.

As substituents for the alkyl group of Y also kationic C2-C5 ammonium derivates are possible, such as e.g. $N(CH_2CH_3)_3$.

Preferably, Y is a linear C1-C7 alkyl group substituted by $NH_2$, $N(CH_3)_2$, $NH(CH_3)$, $N(CH_3)_3$, pyridinyl or imidazolyl. The amphiphilic component more preferably is a linear unsubstituted C10-C20 alkyl-carboxylate or alkyl-sulfate.

One of the gists of the invention thus is to mix or bind, respectively, the bisphosphonate, which, without taking specific measures is too mobile in aqueous solutions due to the strong solubility and which, after the fixture of the implant, would be carried away from the surface too soon, with a second component in a composite salt, which has the consequence that this composite salt, which has a significantly lower solubility in water, and therefore also in the physiological environment after the fixture of the implant, therefore can exert its efficacy at the decisive surface over a significantly longer time span. It is noted that while using the coating according to the invention, the availability of the bisphosphonate present in the coating surprisingly is warranted at the implant surface or in the direct environment of the implant, respectively, during several days to weeks. Surprisingly, this can be achieved by a specific selection of additional components. The amphiphilic component, or the bisphosphonate and the water-soluble ionic polymeric component, respectively, are present as a mixture, preferably as a composite salt (i.e. the amphiphilic component is also ionic) with a low solubility in water, and it shows that by the use of the specific amphiphilic or water-soluble ionic polymeric component, an astonishingly good adhesion of the bisphosphonate on prevalent implant materials is achievable. Preferably, the coating is a dry coating. The present invention is based on the idea that the release of a low-molecular agent from an implant coating into the surrounding, in case of an implant aqueous environment, is significantly determined by its diffusion from the dry layer into the environment, and that this release itself is determined by the solubility of the agent in the surrounding aqueous medium. Bisphosphonates usually are compounds which are well soluble in water, such that one can count with a fast diffusion from a humidification and similarly from a dry coating and therefore with a low retardation of the agent at the place of action. It therefore is one of the main ideas of the present invention to transfer the agent, which originally was already present as a solution or in an easily soluble salt-form and which was used this way according to the state of the art, to a poorly soluble salt-form in a dry layer. The availability of the agent is then determined by a dissolution equilibrium between originally free agent and the agent present in the form of an insoluble salt. If now in the aqueous medium the agent, which, according to the solubility product of the poorly soluble salt-agent is freely available, diffuses out of the coating, the equilibrium is shifted toward the free agent and thereby a gradual release of the agent out of the poorly soluble salt agent occurs. With other words, a dissolution equilibrium is upstream (advanced) with respect to the diffusion equilibrium and the release of the agent out of the poorly soluble salt agent replaces the diffusion as the rate-determining step of the release of the agent. A prerequisite for the use of this concept is the ability of the bisphosphonate to form in aqueous medium poorly soluble salts with corresponding anionic or kationic reaction partners of the amphiphilic ionic or water-soluble ionic polymeric components, respectively, suggested according to the invention.

In said salts of amino-bisphosphonates and the amphiphilic ionic, i.e. anionic component, specifically the long-chain alkane-sulfates, or -carboxylates, the according bisphosphonate forms the kationic component, and the amphiphilic ionic or water-soluble ionic polymeric component, respectively, specifically the according long-chain carboxylate or alkane-sulfate, respectively, forms the anionic component. Furthermore, it has been found that by the simultaneous or subsequent addition of a water-soluble salt, as e.g. a calcium- and/or strontium salt, the solubility of the respective salt of amino-bisphosphonates and long-chain carboxylic acid salts or long-chain alkane-sulfates in water can be further decreased. The use of long-chain carboxylic acids and long-chain alkyl-sulphuric acids instead of the according water-soluble salt forms is also within the scope of the invention.

The invention is further based, as mentioned above, among other things, on the surprising finding that amino-bisphosphonates together with water-soluble ionic polymers, which are derived from as such known biologically compatible (bio-) polymers, form bisphosphonate polymer salts which have a low solubility in water, and which also adhere to non-metallic or metallic surfaces without further layer-forming means or a support (carrier) being necessary. Said salts of amino-bisphosphonates and long-chain carboxylic acids or long-chain alkane-sulfates as well as said bisphosphonate-polymer salts are suited as coatings for non-metallic or metallic surfaces and release bisphosphonate in a retarded fashion in aqueous medium.

It is e.g. an aspect of the invention that said salts of amino-bisphosphonates and long-chain carboxylic acids or long-chain alkane-sulfates, as well as said bisphosphonate-polymer salts can be applied as finely distributed suspensions of water or easily volatile, organic solvents, such as e.g. of chloroform or chloroform-mixtures, by a coating process, therefore for example by dipping, spraying or dripping onto non-metallic or metallic surfaces, whereby they form coatings with a good adhesion.

Preferably, the coating is a coating which is present without an additional support or additional carrier, respectively. With other words, the coating essentially or even completely comprises only said composite salts. This significantly facilitates the production of such implants. Surprisingly, it namely shows that the suggested composite salts can be applied directly as a coating, as opposed to other agents, and that an additional specific support or carrier is not necessary.

The coating can be applied in a suitable solvent by dipping, spraying, or dripping onto the surface to be coated, and after volatilization or evaporation of the solvent a bisphosphonate-containing coating which has a low solubility in water is formed by in situ salt formation.

The coating therefore is preferably, among other things, characterized in that after introduction into the human or animal tissue or into the human or animal bone, respectively, it releases the bisphosphonate in a delayed (retarded, sustained release) fashion over a longer time span into the immediately surrounding environment of the implant, or shows its efficacy in the immediate surrounding environment of the implant, respectively.

According to a first preferred embodiment, the mixture or the composite salt, respectively, has a solubility in pure water of less than 1 mg/ml at room temperature, preferably in the range of 0.05-0.9 mg/ml at room temperature.

As an implant within the meaning of this invention, each support structure shall be understood, which is preferably suitable for use in or embedding in, respectively, and/or on human or animal tissue or bone, respectively. Dental implants are thereby explicitly excluded. The implant can have an even (smooth) or roughened surface. It can be porous or non-porous, the latter with open pores which penetrate the entire structure or with an only superficial porosity. It can be a non-reinforced or reinforced support structure, for example a fibre-reinforced support structure. Such implants can for instance be selected from the group of: vessel prosthesis, bone replacement material, bone support material, scaffold, film, pin, thorn, rack, nail, wire, screw, plate, tube, hose, polymeric foam component with open pore structure, fibre, fabric, prostheses, especially joint prostheses, nets, cages, metal foams, porous metallic and ceramic coatings, allogenic and xenogenic implants, cardiovascular implants, artificial ligaments, artificial invertebral disks, introcorneal and intraocular implants, cochlear prostheses, active implants, electrodes and/or combinations thereof. Furthermore, the implant can even be designed partially or fully bio-degradable.

In principle, support structures are preferred which are supposed to be provided for the animal or human body middle-term or long-term. However, it is also possible to apply the coating according to the invention to structures which are provided in the body only temporarily and possibly only for a timely delayed release of bisphosphonate. Accordingly, the implant according to the invention can also be for instance coated spheres, fibres, fabric, film or similar. Especially in this context, it is also possible to design the actual support structure in a bio-degradable fashion, such that is does not have to be removed post-operatively after the successive release of the agent, but is dissolvable and degradable by the body on its own. Thereby, the coatings according to the invention can be deposited on such bio-degradable materials, for instance after a general invasion in the area of the operated bone, where they successively release the agent as long as it is necessary in this zone, and are subsequently degraded by the body.

A further preferred embodiment is characterized in that the bisphosphonate is an amino-bisphosphonate. Such as for example pamidronic acid, alendronic acid, neridronic acid, risedronic acid, zoledronic acid, olpadronic acid, ibandronic acid, minodronic acid, or cimadronic acid or a mixture and/or alkali- or earth alkali salts thereof. The already known components pamidronic acid and/or alendronic acid have been shown to be especially effective, possibly in the form of the alkali- or earth-alkali salt, such as for example sodium-alendronate, or sodium-pamidronate, respectively. Generally, it is preferred if the bisphosphonate is present in the free phosphonic acid form, the sodium-, potassium-, ammonium-, calcium-, magnesium- and/or strontium salt form.

According to a further preferred embodiment the amphiphilic component, which is the reason for a reduced solubility of the bisphosphonate in the composite salt with the bisphosphonate, is at least one component selected from the group of the linear unsubstituted C10-C20 alkyl-carboxylates or alkyl-sulfates, or their alkali- or earth alkali salts, respectively, preferably laurate, stearate, palmitate, myristate, oleate, behenate, dodecylsulfate, preferably as alkali- or earth alkali salts or mixtures thereof.

According to another preferred embodiment the water-soluble ionic polymeric component, which in the composite salt with the bisphosphonate is the reason for a reduced solubility of the bisphosphonate, is a polymeric component with free anionic groups, preferably a polymeric component, which is derived from biologically compatible biopolymers. Thus, the water-soluble ionic polymeric component can preferably be carboxylated, carboxymethylated, sulphated, or phosphorylated derivates of natural polysaccharides, more preferably of polysaccharides selected from dextran, pullulane, chitosan, starch, or cellulose, or mixtures thereof.

Preferably, the bisphosphonate preferentially selected as amino-bisphosphonate and the amphiphilic component preferentially selected as an alkyl-sulfate or alkyl-carboxylate, are present in the coating in a molar ratio of between 10:1 and 1:5, more preferably in a molar ratio of 2:1 to 1:2. Accordingly, the bisphosphonate selected as amino-bisphosphonate and the water-soluble ionic polymeric component are present in the coating preferably in a molar ratio between 10:1 and 1:5, more preferably in a molar ratio of 2:1 to 1:2, each with respect to the amino groups of the amino group-containing bisphosphonate used and the anionic groups present in the polymeric component.

Such a coating can be applied to an even (smooth), porous and/or roughened surface. The surface structure can therein be produced by mechanical processes (e.g. sand blasting)

and/or by chemical processes (e.g. acid treatment) and/or over chemo-physical processes as e.g. plasma injections.

Basically, this coating is applicable to implants according to the state of the art, such as for example to an implant on a metallic and/or ceramic basis. It thereby shows that the coating is not dependent on a specific underlying layer or an additional support/carrier in order to immobilize the bisphosphonate, which significantly facilitates the production and makes it more cost-efficient. Accordingly, the coating can be applied to such an implant directly and without an intermediate layer. The implant preferably is for example an implant on the basis of calcium-phosphate-ceramics, bioglass, glass-ceramics, calcium-carbonate, calcium-sulfate, organic and preferably absorbable polymers, or composites of said materials, or on the basis of pure titanium, titanium alloys, cobalt-chromium-alloys or stainless steel, or on the basis of native elements such as collagen, gelatine, or materials of allogenic origin.

Preferably, the coating has a thickness in the range of 0.1-10 µm, preferably of 0.5-5 µm.

Furthermore, the present invention concerns a process for the production of an implant, preferably of the type described above. Therein, a suspension or solution, which contains a bisphosphonate of the general formula, as indicated above, as well as at least one amphiphilic component, as indicated above, and/or a water-soluble ionic polymeric component, as mentioned above, is produced, and the coating is applied to the surface to be coated of the implant by dipping, spraying, or dripping of this suspension or solution (or the suspension- or solvent mixture, respectively) and a coating which has a low solubility in water is formed after vaporization or evaporation of the suspension means or solvent (or suspension- or solvent mixture).

The coating can therein either be produced in that in a first coating step a solution, e.g. of an amino-bisphosphonate in a suitable solvent, is applied to the surface to be coated by dipping, spraying or dripping, and that after vaporization or evaporation of the solvent in a second coating step an amphiphilic and/or polymeric component in a suitable solvent is applied to the surface to be coated by dipping, spraying or dripping and that after vaporization or evaporation of the second solvent a bisphosphonate-containing coating, which has a low solubility in water, is formed by in situ salt formation.

However, it is also possible to first produce the two components in an aqueous solution, to precipitate them therefrom and subsequently to apply them by said methods together with a suitable solvent or suspension means. Thereby, for example the bisphosphonate and the amphiphilic component and/or the water-soluble ionic polymeric component can be produced, in that bisphosphonate solubilized in water is mixed with amphiphilic component solubilized in water or water-soluble ionic polymeric component, respectively, and, that possibly after the addition of additional salts, as for example calcium chloride, the precipitation product is isolated as a composite salt, and subsequently this composite salt is solubilized in a suspension means or solvent (e.g. org. solvent, such as chloroform or also water) or a suspension- or solvent mixture or suspended therein, respectively. The additional salt, which is used for the precipitation, can be used therein e.g. at a ratio of bisphosphonate:additional salt of in the range of 1:2 to 2:1.

The drying of the coated implants can be carried out by a known drying process, therefore for example by drying in a gas stream or by the use of vacuum and/or increased temperature. According to the invention, the application of both solutions can also be carried out in the opposite order. Preferably, it is additionally possible to apply the composite salt to a pre-warmed implant, e.g. at a temperature of the implant of more than 70 degrees Celsius.

According to the invention, non-metallic and metallic and native implant surfaces can be coated with the described bisphosphonate-containing compositions. In the first case, materials of aluminium oxide-, zircon-oxide, calcium phosphate ceramics, bioglass or glass ceramics or mixtures of these ceramics and preferably absorbable polymers are especially preferred. In the second case, they are made of pure metals or metal alloys normally used in implant medicine, such as for example pure titanium, titanium alloys, cobalt-chromium-alloys or stainless steel. The native materials can for example also be made of collagen scaffolds or allograft implants.

The use of implants with a structured surface is especially preferred.

According to a preferred embodiment of the method according the invention, the concentrations of the coating solutions containing the amino-bisphosphonate and the amphiphilic and/or the polymeric component, are selected such that in the coating formed by in situ salt formation the (amino-)bisphosphonate and the amphiphilic component or the polymeric component, respectively, are present in a molar ratio between 10:1 and 1:5, preferably between 2:1 and 1:2.

As a suspension means or solvent, or suspension- or solvent mixture, besides water one or more organic suspension means and/or solvents can be used, such as e.g. chloroform as a suspension means or a mixture of chloroform and triethylenglycol in the ratio of 97.5:2.5 as a solvent.

Furthermore, the present invention concerns a bisphosphonate-containing composition with a low solubility in aqueous environment, in the form of a composite salt. This composition contains a bisphosphonate of the general formula $(H_2O_3P)$—$C(X)(Y)$—$(PO_3H_2)$, wherein X is selected from H, OH, Cl, F, or a methyl group, Y is selected from H, Cl, F, $NH_2$, or a linear or a branched C1-C20 alkyl group (preferably C1-C10 or C1-C7), which is unsubstituted or preferably substituted by $NH_2$, $N(CH_3)_2$, $NH(CH_3)$, $N(CH_3)_3$, pyridinyl or imidazolyl, wherein one or more carbon atoms can be replaced by hetero atoms selected from the group $NR^1$, S or O, wherein $R^1$ is selected from H or $CH_3$, with the proviso that no two hetero atoms are interconnected, or pharmaceutically compatible salts or esters of the latter, in addition to at least one amphiphilic component selected from the group of branched or linear, substituted or unsubstituted, saturated or partially unsaturated C10-C30 alkyl-, alkenyl-, alkylaryl-, aryl-, cycloalkyl-, alkylcycloalkyl-, alkylcykloaryl-carboxylates, -phosphates, or -sulfates or mixtures thereof, and/or a water-soluble ionic polymeric component.

Preferably, Y is a linear C1-C7 alkyl group substituted by $NH_2$, $N(CH_3)_2$, $NH(CH_3)$, $N(CH_3)_3$, pyridinyl or imidazolyl. The amphiphilic component more preferably is a linear unsubstituted C10-C20 alkyl-carboxylate or alkyl-sulfate.

The composite salt therein preferably has a solubility in pure water of less than 1 mg/ml at room temperature, more preferably of in the range of less than 0.05-0.9 mg/ml at room temperature. Preferably, the bisphosphonate is an amino-bisphosphonate, preferably pamidronic acid, alendronic acid, neridronic acid, risedronic acid, zoledronic acid, olpadronic acid, ibandronic acid, minodronic acid or cimadronic acid or a mixture and/or alkali- or earth alkali salts thereof, wherein especially pamidronic acid and/or alendronic acid, possibly in the form of the alkali or earth alkali salt is preferred, and that preferentially the bisphosphonate is present in the free phosphonic acid form, the sodium-, potassium-, ammonium-, calcium-, magnesium- and/or strontium salt form.

Furthermore, it is preferred that the amphiphilic component is at least one component selected from the group of the linear unsubstituted C8-C20 alkyl-carboxylates or alkyl-sulfates, or their alkali- or earth alkali salts, respectively, especially preferred laurate, stearate, palmitate, myristate, oleate, behenate, dodecylsulfate, preferably as alkali- or earth alkali salts or mixtures thereof, or the water-soluble ionic polymeric component is a polymeric component with free anionic groups, respectively, especially preferred a polymeric component, which is derived from biologically compatible biopolymers, wherein the water-soluble ionic polymeric component preferably is a carboxylated, carboxymethylated, sulphated or phosphorylated derivative of natural polysaccharides, more preferably polysaccharides selected from dextran, pullulans, chitosan, starch, or cellulose, or mixtures thereof.

Furthermore, the present invention concerns a use of a composition as described above, for the coating of non-metallic, metallic, polymeric, ceramic, or native implant surfaces, wherein the implant surfaces can be even (smooth), structured and/or porous.

Further preferred embodiments of the invention are outlined in the dependent claims.

SHORT DESCRIPTION OF THE FIGURE

The invention shall be further illustrated by embodiments in connection with the FIGURE.

FIG. 1 shows the turning-out torque for implants with various different surfaces.

DETAILED DESCRIPTION OF THE PREFERRED EMBODIMENTS

The following examples are for the purpose of further illustrating the invention without limiting the same. Variations of the introduced embodiments, as they are comprised by the following claims, are available to the person skilled in the art within the scope of his technical professional knowledge, and accordingly the embodiments depicted below shall not be used for the limitation of the scope of protection provided by the claims, but shall only be interpreted for supportive purposes.

Production of an Alendronic Acid Stearate Salt 100 mg (0.3076 mmol) of sodium alendronate are solubilized in 10 ml of water at 80° C. and added to a solution of 94.3 mg (0.3076 mmol) of sodium stearate in 5 ml of water (solubilized at 80° C.). The milky suspension formed thereby is stirred for over 18 hours at 80° C. under inert conditions. The suspension is subsequently centrifuged for 10 min at 14000 U/min. After removal of the supernatant the precipitate is washed with distilled water and is dried in the desiccator under vacuum (10 mbar) at room temperature for at least 2 days. The final product was received with a yield of 30%.

Production of a Calcium Pamidronate Stearate 20 mg (0.0717 mmol) of disodium pamidronate are solubilized in 5 ml of water and 21.97 mg (0.0717 mmol) of sodium stearate in 5 ml of water at 80° C. each. Both clear solutions are mixed and stirred for 30 min at 80° C. After the addition of 1M calcium chloride solution (ratio pamidronate:stearate:$CaCl_2$=1:1:1) a milky white suspension is formed, which is stirred for 18 hours at 80° C. under inert conditions. Subsequently, the precipitate is centrifuged (14000 U/min; 10 min) and the supernatant is removed. The remaining precipitate is washed once with distilled water. The final product is dried in the desiccator under vacuum (10 mbar) for at least 2 days. The calcium pamidronate stearate is received with a yield of 69.3%.

Production of Alendronic Acid Dodecylsulfate 100 mg (0.3076 mmol) of sodium-alendronate are solubilized in 10 ml of water at room temperature and added to a solution of 88.7 mg (0.3076 mmol) of sodium dodecyl sulphate (SDS) in 5 ml of water (solubilized at RT) and stirred for 30 min at room temperature. After the addition of 1M calcium chloride solution at a ratio of alendronate:SDS:$CaCl_2$=1:1:1, a white precipitate is released. The suspension is stirred for an additional 18 hours at room temperature. After centrifugation (14000 U/min; 10 min), the clear supernatant is removed and the precipitate is washed with distilled water. The end product is dried in the desiccator under vacuum (10 mbar) at room temperature for at least 2 days. The achieved yield of alendronic acid dodecylsulfate is 88.4%.

Production of a Calcium Alendronic Acid Carboxymethyldextrane Salt 50 mg (0.15378 mmol) of sodium alendronate (solubilized in 4 ml of water) are mixed with 22.98 mg (0.1038 mmol) of carboxymethyldextrane (CMD) with a substitution degree of 0.74, solubilized in 1 ml of water, and stirred for 30 min at room temperature. After the addition of 1M calcium chloride solution at a ratio of alendronate:CMD:$CaCl_2$=2:1:2, a white, milky precipitate is formed. The suspension was stirred for an additional 18 hours at room temperature. After centrifugation (14000 U/min; 10 min), the clear supernatant is removed and the remaining precipitate is washed with distilled water. The end product is dried in the desiccator under vacuum (10 mbar) at room temperature for at least 2 days. The ratio of alendronate to CMD was varied from 2:1 to 1:2. The yields of the respective approaches were 54.2% for 2:1, 44.8% for 1:1, and 12.2% for 1:2.

Coating of Implants

An implant (hip joint implant) on the basis of titanium was first roughened in the area exposed to the bone by a sand blasting process. Subsequently, a suspension of the above produced alendronic acid stearate salt in chloroform by addition of 0.025 g of the alendronic acid stearate salt to 4.975 g of chloroform (3.3 ml) was produced within 10 min under stirring. By treatment with an ultrasound-homogenizer (20 Watt total capacity) a homogenous suspension was gained.

The implants were warmed to 80° C. and sprayed with the described suspension several times with a conventional spraying pistol (3×). During the spraying process, the implants clamped in a suitable device rotated evenly around their longitudinal axis. Between the spraying cycles the implants were dried at 80° C. until the solvent was completely evaporated.

Experiments with Animals

The implants thus produced showed an ingrowth behaviour free of complications and an improved osteointegration compared to the implants according to the state of the art. Furthermore, a good integration at the soft tissue is shown.

FIG. 1 shows corresponding results of experiments conducted with three different surface implant types. Therein, a titanium implant in the form of a pin with a diameter of 4.2 mm and a length of 8 mm was used. The surfaces of implant (1) were sand blasted and acid etched without any further coating, while the surfaces of implant (2) were oxidized plasmachemically anodically without any further coating and the surfaces of implant (3) were sand blasted and acid etched and coated with a coating essentially according to the above described example concerning the coating of implants (see above: chapter coating of implants) and then the implants (1), (2), and (3) were compared in an animal experiment.

The sand blasted, acid etched surface and the plasma-chemically anodically oxidized surface relate to the surfaces of commercially spread and often used implants.

The implants were implanted into the pelvis of sheep. After a recovery period of 2 weeks, the turning-out torque necessary in order to release the ingrown implants from the bone was determined in Nmm. As FIG. 1 shows, a significantly improved ingrowth of the implant (3) coated according to the invention is achieved.

The invention claimed is:

1. A non-dental implant, which comprises:
   an implant body having at least one surface area which is to be in direct or indirect contact with hard and/or soft tissue, and
   a coating at least in surface areas of the implant body which are at least in indirect contact with hard and/or soft tissue when implanted, wherein the coating consists of:
   an amino-bisphosphonate of the general formula

   (H$_2$O$_3$P)—C(X)(Y)—(PO$_3$H$_2$)   (I)

wherein
   X is selected from a group consisting of H, OH, Cl, F, and a methyl group, and
   Y is a linear C1-C7 alkyl group substituted by a group selected from NH$_2$, N(CH$_3$)$_2$, NH(CH$_3$), N(CH$_3$)$_3$, pyridinyl, imidazolyl, or pharmaceutically compatible salts and esters thereof, and
   at least one amphiphilic component that is a linear unsubstituted C10-C20 alkyl-carboxylate or alkyl-sulfate and mixtures thereof;
   wherein the coating is a composite salt having a solubility in pure water of less than 1 mg/ml;
   wherein, in the coating, the amino-bisphosphonate and the amphiphilic component are present as the composite salt directly on a surface of the implant body without an intermediate layer between the surface of the implant body and the coating, wherein the surface of the implant body is even, porous and/or roughened;
   wherein amino-bisphosphonate and the amphiphilic component are present in the coating in a molar ratio between 2:1 and 1:2; and
   wherein the coating has a thickness in the range of 0.1-5 μm; and
   wherein the implant body is selected from the group consisting of bioglass, glass ceramics, calcium carbonate, calcium sulphate, organic polymers, pure titanium, titanium alloys, cobalt-chromium alloys, stainless steel, or composites thereof, and native implant surfaces, wherein the native implant surfaces are composed of collagen, gelatine or materials of allogenic origin.

2. The implant according to claim 1, wherein the amino-bisphosphonate is selected from the group consisting of: pamidronic acid, alendronic acid, neridronic acid, risedronic acid, zoledronic acid, olpadronic acid, ibandronic acid, minodronic acid, cimadronic acid, alkali-salts thereof, earth alkali-salts thereof, and mixtures thereof.

3. The implant according to claim 1, wherein the amino-bisphosphonate is present in at least one of the free phosphonic acid form, the sodium-, potassium-, ammonium-, calcium-, magnesium- and/or strontium-salt form.

4. The implant according to claim 1, wherein the amphiphilic component is selected from the group consisting of: laurate, stearate, palmitate, myristate, oleate, behenate, dodecylsulfate, alkali-salts thereof, earth alkali-salts and mixtures thereof.

5. The implant according to claim 1, wherein the coating is operative, after introduction of the implant body into human or animal tissue, or human or animal bone, respectively, to release the amino-bisphosphonate in a delayed manner.

6. The implant according to claim 1, wherein the implant coating is a dry, essentially solvent-free and essentially water-free coating.

7. The implant according to claim 1, wherein the amphiphilic component has a monovalent or bivalent negative charge.

8. The implant according to claim 1, wherein the coating has been applied as a slurry or suspension in an organic solvent.

9. The implant according to claim 1, wherein the composite salt has a solubility in pure water in the range of 0.05-0.9 mg/ml at room temperature.

10. The implant according to claim 1, wherein the coating is applied as a slurry or suspension in an organic solvent, in a spraying- or dipping process and subsequently completely dried.

11. A non-dental implant, which comprises:
    an implant body having at least one surface area which is to be in direct or indirect contact with hard and/or soft tissue, and
    a coating at least in surface areas of the implant body which are at least in indirect contact with hard and/or soft tissue when implanted, wherein the coating consists of:
    an amino-bisphosphonate of the general formula

    (H$_2$O$_3$P)—C(X)(Y)—(PO$_3$H$_2$)   (I)

wherein
    X is selected from a group consisting of H, OH, Cl, F, and a methyl group, and
    Y is a linear C1-C7 alkyl group substituted by a group selected from NH$_2$, N(CH$_3$)$_2$, NH(CH$_3$, N(CH$_3$)$_3$, pyridinyl, imidazolyl, or pharmaceutically compatible salts and esters thereof, and
    a water-soluble ionic polymeric component with free anionic groups, which is a carboxylated, carboxymethylated, sulphated or phosphorylated derivative of natural polysaccharides;
    wherein the coating is a composite salt having a solubility in pure water of less than 1 mg/ml;
    wherein, in the coating, the amino-bisphsphonate and the water-soluble ionic polymeric component are present as the composite salt directly on a surface of the metal or ceramic implant body without an intermediate layer and as a composite salt of low solubility in water, wherein the surface of the implant body is even, porous and/or roughened;
    wherein the amino-bisphosphonate and the water-soluble ionic polymeric component are present in the coating in a molar ratio between 2:1 and 1:2, each with respect to the amino groups of the amino group-containing bisphosphonate used and the anionic groups of the polymeric component which are present;
    wherein the coating has a thickness in the range of 0.1-5 μm; and
    wherein the implant body is selected from the group consisting of bioglass, glass ceramics, calcium carbonate, calcium sulphate, organic polymers, pure titanium, titanium alloys, cobalt-chromium alloys, stainless steel, or composites thereof, and native implant surfaces, wherein the native implant surfaces are composed of collagen, gelatine or materials of allogenic origin.

12. The implant according to claim 11, wherein the amino-bisphosphonate is selected from the group consisting of: pamidronic acid, alendronic acid, neridronic acid, risedronic acid, zoledronic acid, olpadronic acid, ibandronic acid, minodronic acid, cimadronic acid, alkali-salts thereof, earth alkali-salts thereof, and mixtures thereof.

13. The implant according to claim 11, wherein the amino-bisphosphonate is present in at least one of the free phosphonic acid form, the sodium-, potassium-, ammonium-, calcium-, magnesium- and/or strontium-salt form.

14. The implant according to claim 11, wherein the coating is operative, after introduction of the implant body into human or animal tissue, or human or animal bone, respectively, to release the amino-bisphosphonate in a delayed manner.

15. The implant according to claim 11, wherein the implant coating is a dry, essentially solvent-free and essentially water-free coating.

16. The implant according to claim 11, wherein the coating has been applied as a slurry or suspension in an organic solvent.

17. The implant according to claim 11, wherein the composite salt, has a solubility in pure water in the range of 0.05-0.9 mg/ml at room temperature.

18. The implant according to claim 11, wherein the implant body is selected from the group consisting of: vessel prosthesis, bone replacement material, bone support material, scaffold, film, pin, thorn, rack, nail, wire, screw, plate, tube, hose, polymeric foam component with open pore structure, fibre, fabric, prostheses, nets, cages, metal foams, porous metallic and ceramic coatings, allogenic and xenogenic implants, cardiovascular implants, artificial ligaments, artificial intervertebral discs, intra-corneal and intraocular implants, cochlear prostheses, active implants, electrodes and combinations thereof.

19. The implant according to claim 11, wherein the coating is applied as a slurry or suspension in an organic solvent, in a spraying- or dipping process and subsequently completely dried.

* * * * *